(12) United States Patent
Levine

(10) Patent No.: US 7,789,227 B2
(45) Date of Patent: Sep. 7, 2010

(54) STORAGE AND MIXING DEVICE

(76) Inventor: Jonathan E. Levine, 419 Park Ave., Suite 1302, New York, NY (US) 10016

(*) Notice: Subject to any disclaimer, the term of this patent is extended or adjusted under 35 U.S.C. 154(b) by 839 days.

(21) Appl. No.: 11/649,300

(22) Filed: Dec. 28, 2006

(65) Prior Publication Data
US 2008/0156673 A1 Jul. 3, 2008

(51) Int. Cl.
B65D 25/08 (2006.01)
A01M 13/00 (2006.01)

(52) U.S. Cl. .................. 206/221; 206/219; 206/568; 206/822; 222/138; 119/677; 43/125

(58) Field of Classification Search .................. 206/219, 206/221, 568, 0.6, 439; 215/DIG. 8; 220/4.21, 220/4.24, 4.25, 23.2, 23.4, 23.8, 23.83, 253, 220/259.1, 259.2, 259.5, 345.5, 501, 502, 220/525, 745, 747, 749, 750, 4.06, 4.07; 366/204; 222/138, 142.2, 144; 423/477–480; 119/677; 422/164, 305; 43/125, 127
See application file for complete search history.

(56) References Cited

U.S. PATENT DOCUMENTS

| | | | |
|---|---|---|---|
| 4,779,722 A * | 10/1988 | Hall ........................... 206/221 |
| 5,278,112 A | 1/1994 | Klatte |
| 5,314,852 A | 5/1994 | Klatte |
| 5,464,598 A | 11/1995 | Klatte |
| 5,567,405 A | 10/1996 | Klatte et al. |
| 5,573,743 A | 11/1996 | Klatte et al. |
| 5,725,645 A * | 3/1998 | Wickland et al. ........ 206/524.8 |
| 5,730,948 A | 3/1998 | Klatte et al. |
| 5,776,850 A | 7/1998 | Klatte et al. |
| 5,853,689 A | 12/1998 | Klatte |
| 5,883,739 A | 3/1999 | Ashihara et al. |
| 5,885,543 A | 3/1999 | Klatte |
| 5,901,851 A * | 5/1999 | Charpentier ................ 206/581 |
| 6,174,508 B1 | 1/2001 | Klatte |
| 6,379,643 B1 | 4/2002 | Klatte |
| 6,423,277 B1 | 7/2002 | Gravitt et al. |
| 6,423,289 B1 | 7/2002 | Klatte |
| 6,458,735 B1 | 10/2002 | Klatte |
| 6,503,419 B2 | 1/2003 | Klatte |
| 6,945,393 B2 | 9/2005 | Cho |
| 7,083,043 B2 | 8/2006 | Sharon |
| 2005/0087457 A1* | 4/2005 | Schmidt et al. ............. 206/219 |
| 2006/0049127 A1* | 3/2006 | Katz et al. ............. 215/DIG. 8 |

FOREIGN PATENT DOCUMENTS

JP          02009330 A  *  1/1990

* cited by examiner

Primary Examiner—J. Gregory Pickett
(74) Attorney, Agent, or Firm—Theodore W. Baker

(57) ABSTRACT

A handheld storage and mixing device is disclosed. The device can include first and second separate containers each defining a distinct internal cavity. The first container can be movable (e.g., rotatable) relative to the second container between a first position and a second position. In the first position, the cavities can be substantially sealed from one another. In the second position, a first gas forming ingredient in one of the cavities can mix with a second gas forming ingredient in the other cavity to form a gas, such as chlorine dioxide gas. The device can have one or more filtered openings to allow gas generated by mixing the first and second gas forming ingredients to escape into the ambient environment.

25 Claims, 8 Drawing Sheets

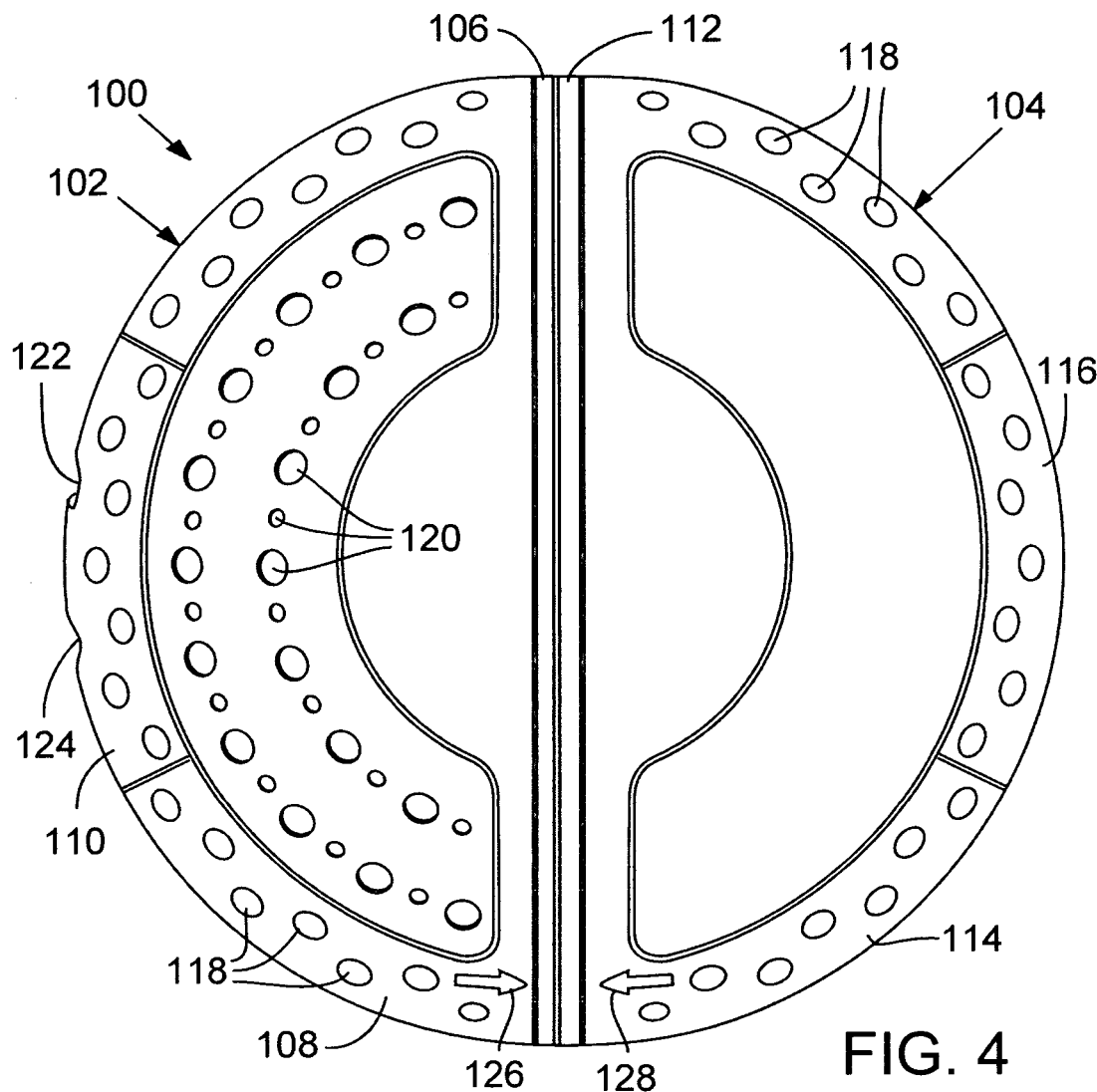
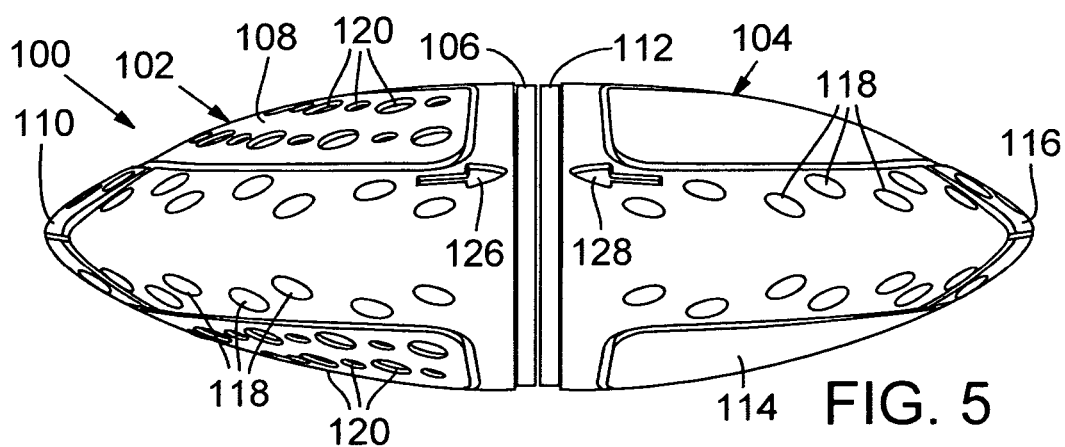

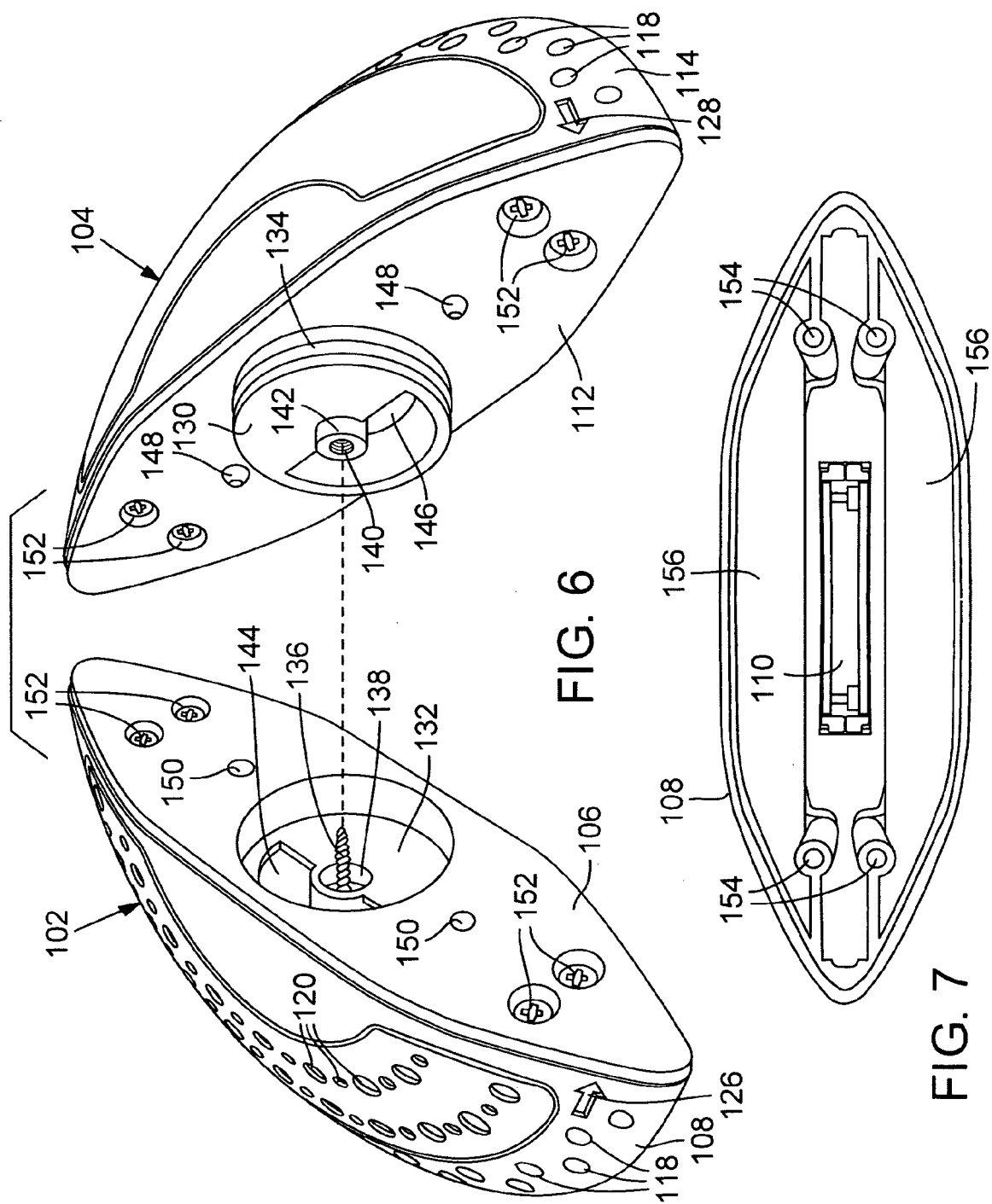

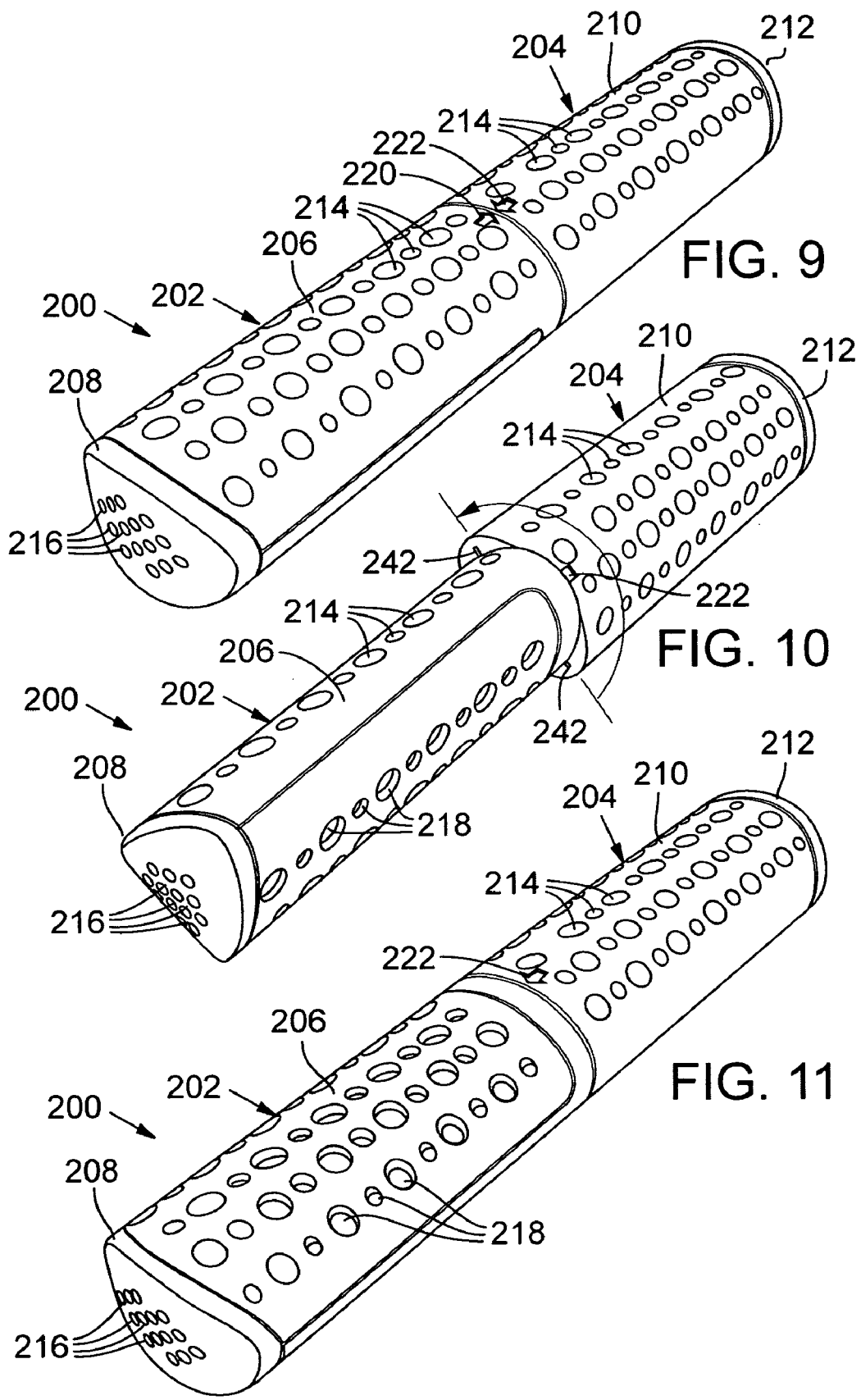

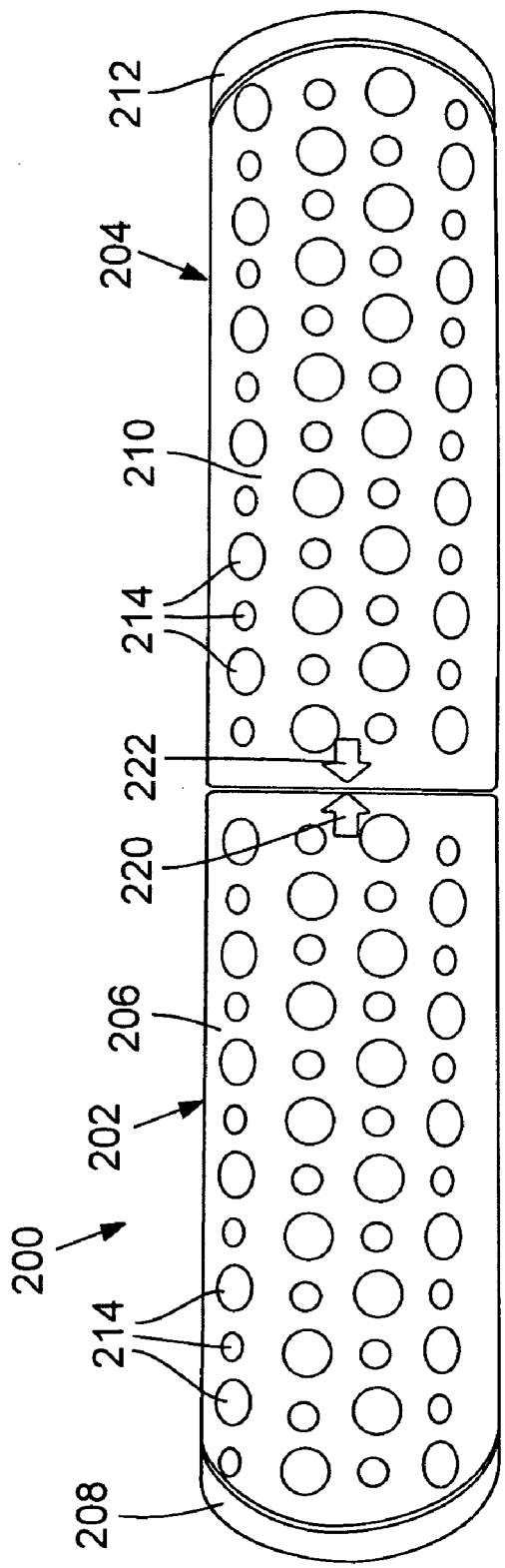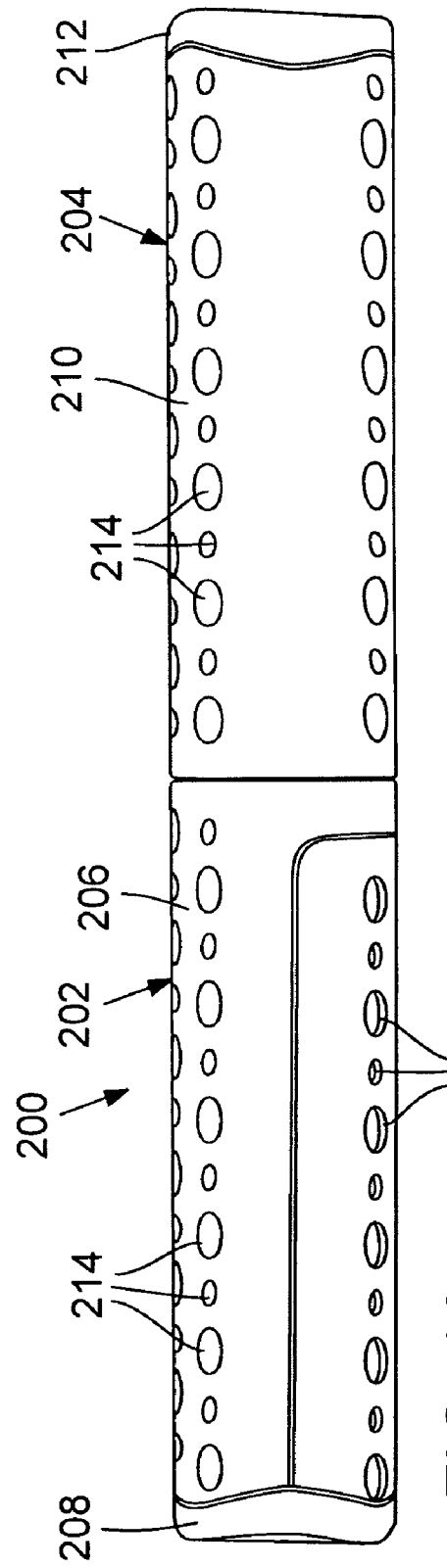

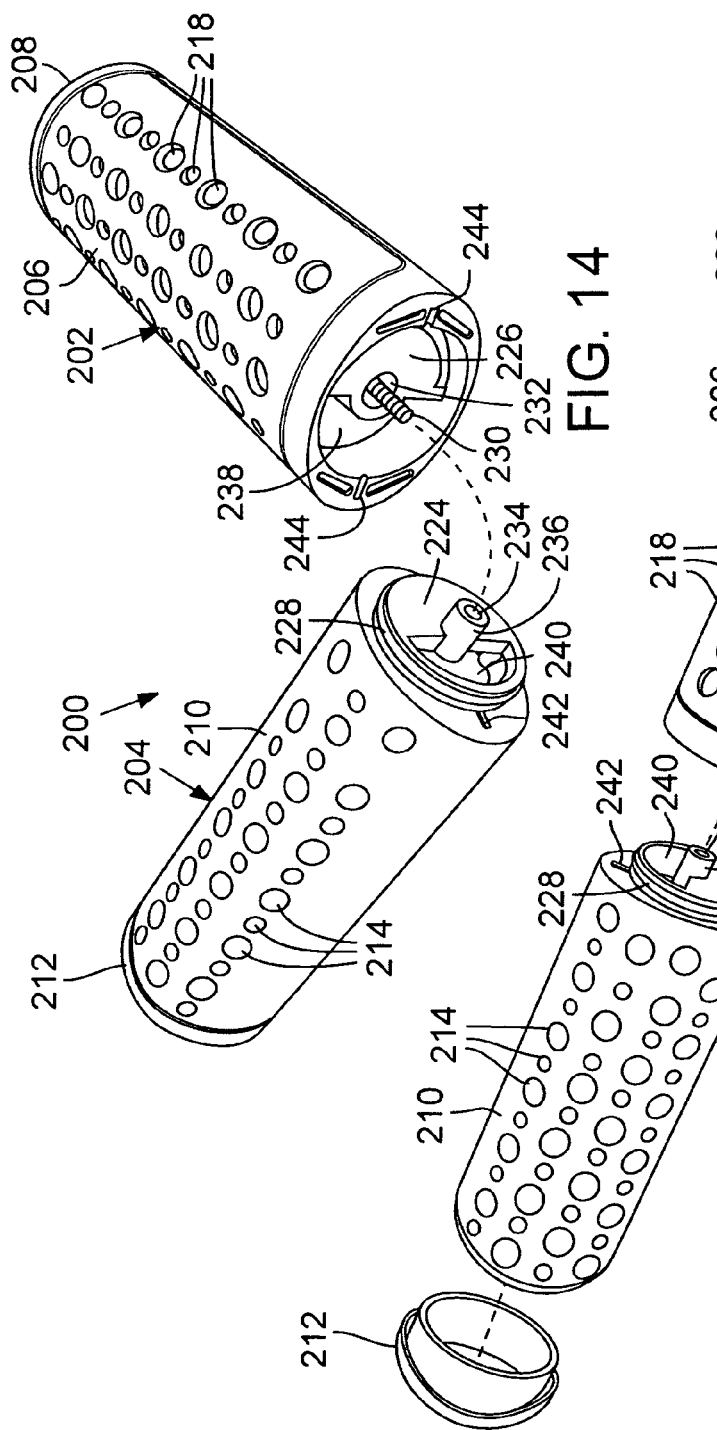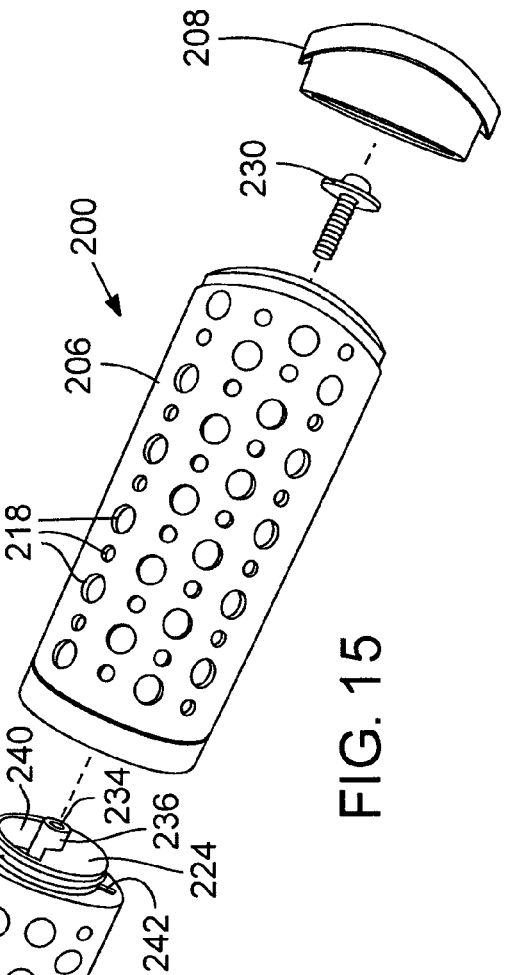

STORAGE AND MIXING DEVICE

FIELD

This disclosure concerns portable mixing devices, such as containers having internal cavities for separately storing two or more components to be mixed.

BACKGROUND

For certain applications, it is useful to separately store two or more components and then mix the components on demand. For example, two or more reactants can be separately stored and then mixed to cause a chemical reaction. In this way, the reaction can be performed on demand to produce, for example, warming, cooling, or formation of a particular reaction product. Forming a reaction product in this manner is especially useful if the reaction product is unstable and difficult to transport.

Chlorine dioxide gas is one example of a useful chemical that is difficult to store and transport and, therefore, typically is formed at its point-of-use. When stored at moderately high concentrations (e.g., greater than about 15% by volume), chlorine dioxide can explosively react to form chlorine and oxygen. Chlorine dioxide often is used for large-scale bleaching and disinfection. For example, chlorine dioxide has been used to decontaminate houses and buildings containing harmful mold or bacteria.

Some examples of containers having multiple chambers for separately storing components to be mixed are known. For example, U.S. Pat. No. 7,083,043 (Sharon) and U.S. Pat. No. 6,945,393 (Cho) disclose such containers. The containers disclosed in Sharon and Cho, however, have limited utility and would be ineffective if used for point-of-use generation of gases, such as chlorine dioxide.

SUMMARY

Disclosed herein are embodiments of a handheld storage and mixing device. Some embodiments include first and second separate containers each defining a distinct internal cavity. The first container can be movable (e.g., rotatable) relative to the second container between a first position and a second position. In some embodiments, the first container is permanently attached to the second container at an axis of rotation. In the first position, the cavities can be substantially sealed from one another. In the second position, a first gas forming ingredient in one of the cavities can mix with a second gas forming ingredient in the other cavity to form a gas. The first and second gas forming ingredients can be, for example, mixable to form chlorine dioxide gas. The device can have one or more filtered openings to allow gas generated by mixing the first and second gas forming ingredients to escape into the ambient environment. In some embodiments, in the first position, one of the first and second containers is substantially sealed against air infiltration and the other of the first and second containers includes the one or more filtered openings.

The first and second containers can have opposing faces, each with an opening. In the first position the openings can be substantially non-overlapping and in the second position the openings can be substantially overlapping. The opposing faces can have non-circular perimeters. One of the first and second faces can include a cylindrical projection sized to fit within a corresponding cylindrical recess in the other of the first and second faces, and the openings can be positioned on respective end portions of the cylindrical projection and the cylindrical recess. An o-ring can be positioned around a side portion of the cylindrical projection. In some embodiments, the first and second gas forming ingredients cannot be accessed without breaking the device.

The disclosed device can be substantially shaped, for example, as an oblate spheroid or a cylinder. In embodiments in which the device is substantially shaped as a cylinder, the one or more filtered openings can be positioned on an end of the cylinder. In these and other embodiments, the one or more filtered openings can be positioned on a rounded surface. Each of the first and second containers can have an outer surface with an alignment indicator. These alignment indicators can be substantially coplanar when the first container is in one of the first and second positions and substantially non-coplanar when the first container is in the other of the first and second positions. Some embodiments of the device include an opening configured to receive a string.

Some embodiments of the disclosed handheld storage and mixing device include a first container which defines a first face with a first opening and a second container which defines a second face with a second opening. The first and second containers can be substantially shaped as respective halves of an oblate spheroid. The first container can be connected to the second container with the first face substantially parallel to the second face. The first and second containers can be rotatable relative to one another. For example, in a first position, a perimeter of the first face can be substantially aligned with a perimeter of the second face, while the first opening is out of alignment with the second opening and an internal cavity of the first container is separate from an internal cavity of the second container. Starting from the first position, rotating the first container 180 degrees relative to the second container can cause the perimeter of the first face to move out of alignment with the perimeter of the second face and then back into alignment with the perimeter of the second face. At 180 degrees of rotation, the first opening can be substantially aligned with the second opening and the internal cavity of the first container can be open to the internal cavity of the second container.

Embodiments of the disclosed device can include a solid container other than a sphere formed by two connected container halves. Each container half can define a cavity and have an interface surface. The interface surfaces of the container halves can be substantially the same shape and symmetrical with respect to bisecting vertical and horizontal planes. In addition, the interface surfaces can substantially align with one another both in a first orientation and in a second orientation in which one of the interface surfaces is rotated 180 degrees relative to the other. When not disposed in either the first or second orientation, the interface surfaces can be out of alignment.

Also disclosed are embodiments of a method for making a handheld storage and mixing device. These embodiments can include providing a first container and a second container, each having a mixing opening and a loading opening. The first container then can be connected to the second container, such that the mixing openings can be moved into or out of alignment by rotating the first container relative to the second container. A first gas forming ingredient can be introduced into the first container via the first container's loading opening. Similarly, a second gas forming ingredient can be introduced into the second container via the second container's loading opening. The first and second gas forming ingredients can be combinable to form chlorine dioxide gas. The loading openings of the first and second containers also can be sealed, such as by placing a cover over each loading opening and welding the cover to the respective container.

Also disclosed are embodiments of a method for performing a chemical reaction. The method can include providing a handheld storage and mixing device comprising a first container and a second container and rotating the first container relative to the second container to open a connection between the first and second containers. The method also can include agitating the device, such that a first gas forming ingredient in the first container mixes with a second gas forming ingredient in the second container to form a gas. The gas can be released via filtered perforations. In some embodiments, the gas is chlorine dioxide and the method also includes placing the device in an area in need of deodorizing or disinfection after agitating the device.

BRIEF DESCRIPTION OF THE DRAWINGS

FIG. 4 is a plan view of the storage and mixing device embodiment of FIG. 1.

FIG. 5 is a profile view of the storage and mixing device embodiment of FIG. 1.

FIG. 6 is a partially exploded perspective view of the storage and mixing device embodiment of FIG. 1 showing the interface between the two sections.

FIG. 7 is a profile view of one section of the storage and mixing device embodiment of FIG. 1 with its face plate removed.

FIG. 9 is a perspective view of a second embodiment of the disclosed storage and mixing device with two sections each having an internal cavity and the sections oriented such that the cavities are substantially isolated from one another.

FIG. 10 is a perspective view of the storage and mixing device embodiment of FIG. 9 with one section rotated on a central axis approximately 90 degrees relative to its position in FIG. 9.

FIG. 11 is a perspective view of the storage and mixing device embodiment of FIG. 9 with one section rotated on a central axis approximately 180 degrees relative to its position in FIG. 9 such that the internal cavities are in communication with one another.

FIG. 12 is a plan view of the storage and mixing device embodiment of FIG. 9.

FIG. 13 is a profile view of the storage and mixing device embodiment of FIG. 9.

FIG. 14 is a partially exploded perspective view of the storage and mixing device embodiment of FIG. 9 showing the interface between the two sections.

FIG. 15 is an exploded perspective view of the storage and mixing device embodiment of FIG. 9 showing the interrelationship of the primary components.

DETAILED DESCRIPTION

Described herein are embodiments of a storage and mixing device, embodiments of a method for making the storage and mixing device, and embodiments of a method for performing a chemical reaction. Throughout this disclosure, the singular terms "a," "an," and "the" include plural referents unless the context clearly indicates otherwise. Similarly, the word "or" is intended to include "and" unless the context clearly indicates otherwise. Directional terms, such as "upper," "lower," "front," "back," "vertical," and "horizontal," are used herein to express and clarify the relationship between various elements. It should be understood that such terms do not denote absolute orientation (e.g., a "vertical" component can become horizontal by rotating the device). With respect to the dimples and perforations described below, the lead lines in the figures point to representative examples only.

Figure 1:
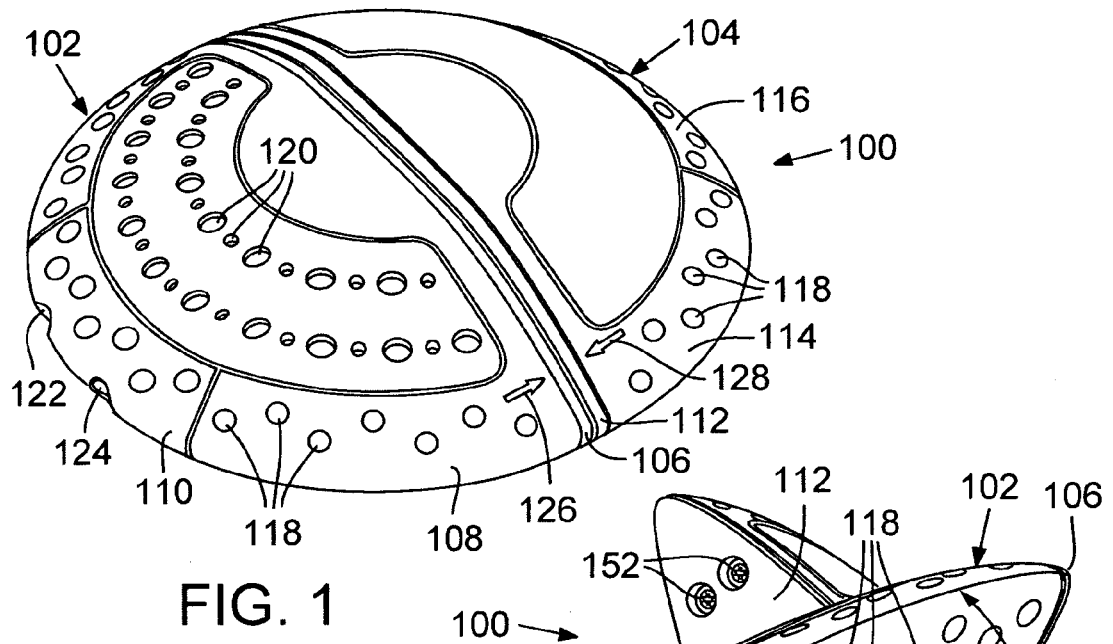
FIG. 1 is a perspective view of a first embodiment of the disclosed storage and mixing device with two sections each having an internal cavity and the sections oriented such that the cavities are substantially isolated from one another.

FIGS. 1-8 show one embodiment of the disclosed storage and mixing device. As shown in FIG. 1, the device 100 includes a first section 102 and a second section 104. The first section 102 includes a first face plate 106, a first shell 108, and a first plug 110. Similarly, the second section 104 includes a second face plate 112, a second shell 114, and a second plug 116. An outer surface of the first section 102 includes dimples 118 and perforations 120. An outer surface of the second section 104 includes dimples 118 and no perforations 120. On an outside edge of the first plug 110, a continuous passage extends from a first string opening 122 to a second string opening 124. In some implementations, an elongated, flexible member (e.g., a string) is routed through this passage. For example, the device 100 can be attached to a string loop in this manner.

Figure 2:
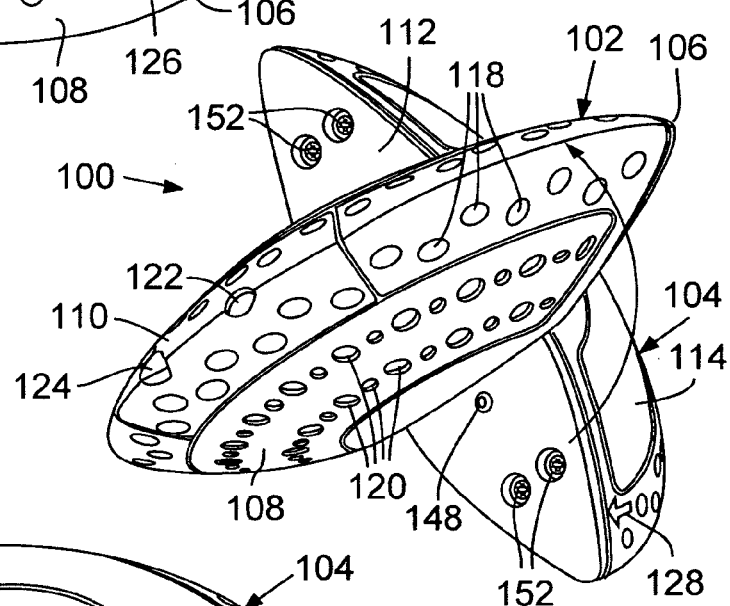
FIG. 2 is a perspective view of the storage and mixing device embodiment of FIG. 1 with one section rotated on a central axis approximately 90 degrees relative to its position in FIG. 1.
Figure 3:
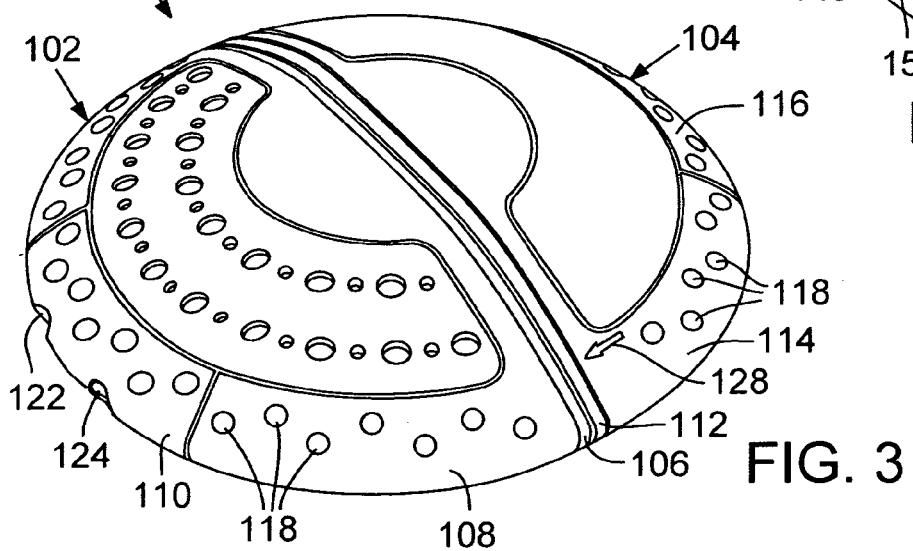
FIG. 3 is a perspective view of the storage and mixing device embodiment of FIG. 1 with one section rotated on a central axis approximately 180 degrees relative to its position in FIG. 1 such that the internal cavities are in communication with one another.

As shown in FIG. 2, the first and second sections 102, 104 can rotate relative to each other on a central axis. The outer surfaces of the first and second sections 102, 104 include respective first and second alignment indicators 126, 128 (shown as arrows in the illustrated embodiment). With the device 100 in a first configuration shown in FIG. 1, the first and second alignment indicators 126, 128 are substantially coplanar and in close proximity. Rotation of the first section 102 relative to the second section 104, as shown in FIG. 2, reorients the device 100 into a second configuration shown in FIG. 3. In the second configuration, the first and second alignment indicators 126, 128 are positioned on opposite sides of the device 100. The relative positions of the first and second alignment indicators 126, 128, therefore, can be used to visually identify whether the device 100 is in the first configuration or the second configuration. Other embodiments may include alignment indicators that are substantially coplanar when the device is in the second configuration rather than in the first configuration.

FIG. 6 is a partially exploded view showing the interface between the first and second sections 102, 104. As shown in FIG. 6, the second face plate 112 includes a cylindrical projection 130. The first face plate 106 includes a corresponding cylindrical recess 132. An o-ring 134 is positioned around a side portion of the cylindrical projection 130 so as to form a tight seal when the device 100 is assembled with the cylindrical projection positioned within the cylindrical recess 132. To connect the first section 102 to the second section 104, a central screw 136 extends through a secondary recess 138 centered on an end portion of the cylindrical recess 132 and into a threaded opening 140 in a secondary projection 142 centered on an end portion of the cylindrical projection 130. The central screw 136 makes no threaded connection to the first face plate 106, so the first section 102 is free to rotate relative to the second section 104 and the central screw.

The first and second sections 102, 104 each define an internal cavity. The end portion of the cylindrical recess 132 includes a first opening 144 to the internal cavity of the first section 102. Similarly, the end portion of the cylindrical projection 130 includes a second opening 146 to the internal cavity of the second section 104. The first and second openings 144, 146 are shaped substantially as semicircles. When the device 100 is in the first configuration, with the first and second alignment indicators 126, 128 substantially coplanar, the first and second openings 144, 146 are not aligned. Instead, the first opening 144 is blocked by the portion of the end portion of the cylindrical projection 130 not occupied by the second opening 146 and the second opening is blocked by the portion of end portion of the cylindrical recess 132 not occupied by the first opening. Thus, in the first configuration, the internal cavities of the first and second sections 102, 104 are sealed from each other. When the first and second sections 102, 104 are rotated relative to one another, the first and second openings 144, 146 move into alignment. In the second configuration, the first and second openings 144, 146 are substantially aligned, such that the internal cavities of the first and second sections 102, 104 are open to one another.

The second face plate 112 includes two bumps 148 that fit into corresponding indentations 150 on the first face plate 106 when the device 100 is in either the first configuration or the second configuration. Typically, an end user will receive the device 100 in the first configuration and then manipulate the first and second sections 102, 104 to place the device in the second configuration to activate the device. The indentations 150 and bumps 148 provide the user with a tactile feel indicating that the first and second face plates 106, 112 are aligned with one another. Although the first and second face plates 106, 112 in the illustrated embodiment are flat, in other embodiments, they can be curved. As best shown in FIG. 2, when the first section 102 is rotated, the cylindrical projection 130 and the cylindrical recess 132 are always covered by the opposing face plate. Some portions of the first and second face plates 106, 112, however, do become exposed. In the illustrated embodiment, these portions include face plate screws 152 attaching the first and second face plates 106, 112 to the first and second shells 108, 114, respectively. Exposing the face plate screws 152 in this way allows the device 100 to be disassembled without the need to break any components. In other embodiments, the face plates are attached to the shells in a manner than does not allow separation of these components after the device is assembled. For example, the face plates can be welded to the shells. This is useful if it is preferable to discourage end users from disassembling the device and releasing the contents of one or more of the internal cavities.

FIG. 7 is a profile view of the internal cavity of the first section 102. The first shell 108 and the first plug 110 are shown without the first face plate 106. Four screw-receiving columns 154 are attached to an inside wall of the first shell 108 to receive the face plate screws 152. In embodiments in which the first face plate 106 is attached by another method, the screw-receiving columns 154 can be eliminated. Two pieces of filter paper 156 line the major internal surfaces of the first shell 108 below the perforations 120. If the cavity contains a solid media with a grain size larger than the pore size of the filter paper 156, the solid media will be contained, but gas will be able to enter into and exit from the cavity via the perforations 120. The second section 104 of the device 100 has no perforations 120, so filter paper 156 is not necessary on an internal surface of the second shell 108. Aside from this difference, the internal cavity of the second section 104 is similar to the internal cavity of the first section 102, as shown in FIG. 7.

Figure 8:
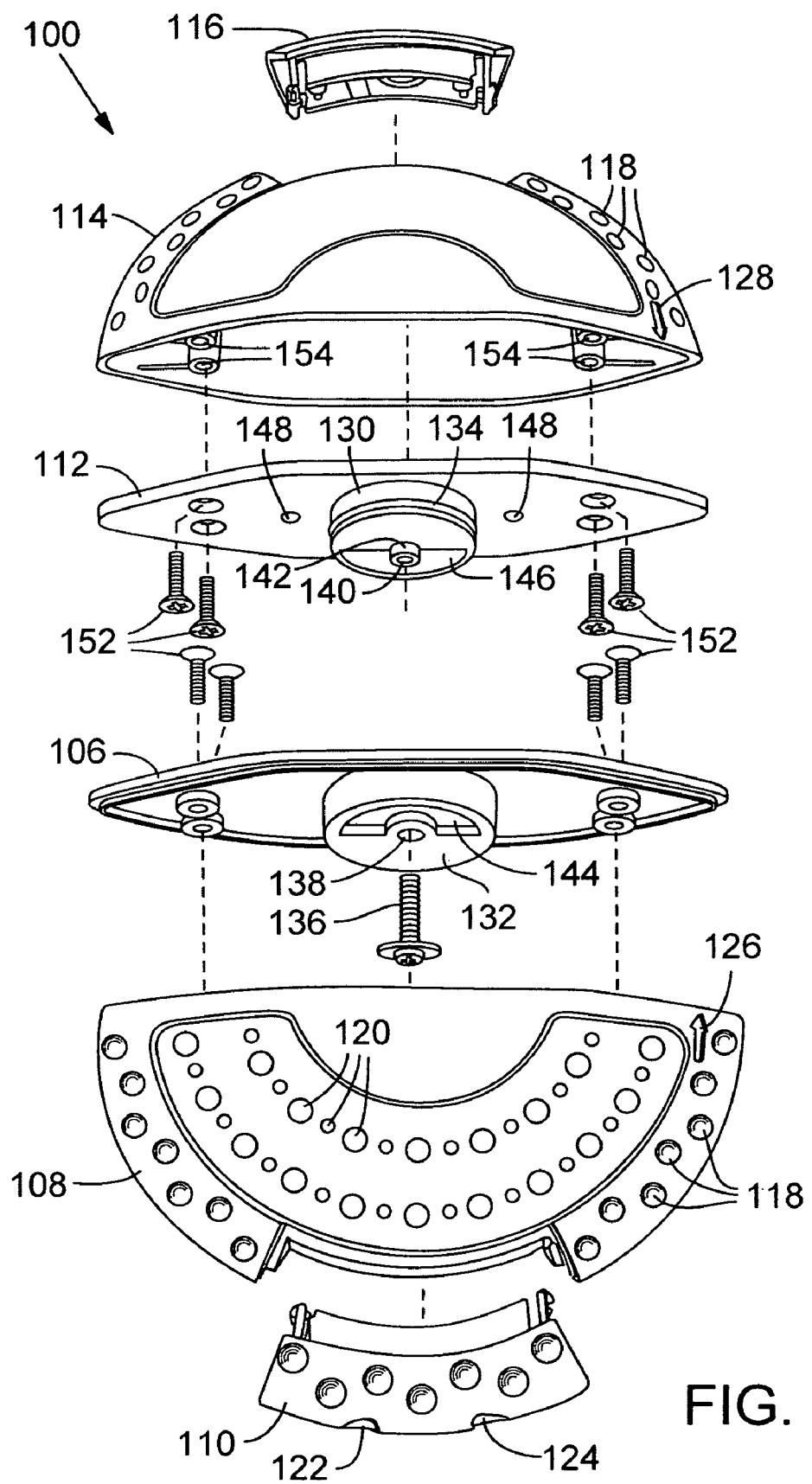
FIG. 8 is an exploded perspective view of the storage and mixing device embodiment of FIG. 1 showing the interrelationship of the primary components.

FIG. 8 is an exploded view of the device 100. As shown in FIG. 8, the first and second plugs 110, 116 can be separated from the first and second shells 108, 114, respectively. In the process of making the device 100, after the first and second face plates 106, 112, have been attached to the first and second shells 108, 114, respectively, and attached to each other by the central screw 136, the internal cavities can be partially or fully filled with media prior to placement of the first and second plugs 110, 116. After the media has been introduced and the first and second plugs 110, 116 have been put into place, the first and second plugs can be permanently attached to the first and second shells 108, 114, respectively, such as by welding. Similar to attachment of the first and second face plates 106, 112 to the first and second shells 108, 114, respectively, as discussed above, permanently attaching the first and second plugs 110, 116 to the first and second shells 108, 114, respectively, prevents end users from accessing the contents of the internal cavities. After attaching the first and second face plates 106, 112 and the first and second plugs 110, 116 to the first and second shells 108, 114, respectively, the first and second sections 102, 104 become permanently attached because there is no way to access the central screw 136 without breaking the device 100.

FIGS. 9-15 show another embodiment of the disclosed storage and mixing device. As shown in FIG. 9, the device 200 includes a first section 202 and a second section 204. The first section 202 includes a first shell 206 and a first cap 208. Similarly, the second section 204 includes a second shell 210 and a second cap 212. The upward facing sides of the first and second sections 202, 204 in FIG. 1 both include dimples 214. The first cap 208 includes cap perforations 216, whereas the second cap 208 is not perforated. Similar to the device 100, beginning in a first configuration shown in FIG. 9, the first section 202 can be rotated relative to the second section 204 to reorient the device 200 into a second configuration shown in FIG. 11. FIG. 10 shows the rotation in progress. In the second configuration, the upward facing side of the first section 202 includes shell perforations 218 and some dimples 214 near the first cap 208. In contrast, the upward facing side of the second section 204 includes dimples 214 only. As with the device 100, first and second alignment indicators 220, 222 on the first and second shells 206, 210, respectively, can be used to visually identify whether the device 200 is in the first configuration or the second configuration.

FIG. 14 is a partially exploded view showing the interface between the first and second sections 202, 204. Unlike the device 100, the first and second shells 206, 210 contact each other directly with no intervening face plates. At its connecting end, the second shell 210 includes a cylindrical projection 224 that fits into a cylindrical recess 226 at a connecting end of the first shell 206. An o-ring 228 is positioned around a side portion of the cylindrical projection 224 so as to form a tight seal when the device 200 is assembled with the cylindrical projection positioned within the cylindrical recess 226. To connect the first section 202 to the second section 204, a central screw 230 extends through a secondary recess 232 centered on an end portion of the cylindrical recess 226 and into a threaded opening 234 in a secondary projection 236 centered on an end portion of the cylindrical projection 224. The central screw 230 makes no threaded connection to the first shell 206, so the first section 202 is free to rotate relative to the second section 204 and the central screw.

The first and second sections 202, 204 each define an internal cavity. The end portion of the cylindrical recess 232 includes a first opening 238 to the internal cavity of the first section 202. Similarly, the end portion of the cylindrical projection 224 includes a second opening 240 to the internal cavity of the second section 204. The first and second openings 238, 240 are shaped substantially as semicircles. When the device 200 is in the first configuration, with the first and second alignment indicators 220, 222 substantially coplanar, the first and second openings 238, 240 are not aligned. Instead, the first opening 238 is blocked by the portion of the end portion of the cylindrical projection 224 not occupied by the second opening 240 and the second opening is blocked by the portion of the end portion of the cylindrical recess 226 not occupied by the first opening. Thus, in the first configuration, the internal cavities of the first and second sections 202, 204 are sealed from each other. When the first and second sections 202, 204 are rotated relative to one another, the first and second openings 238, 240 move into alignment. In the second configuration, the first and second openings 238, 240 are substantially aligned, such that the internal cavities of the first and second sections 202, 204 are open to one another.

The connecting end of the second shell 210 includes two rectangular projections 242 (one shown in FIG. 14) that fit into corresponding indentations 244 on the connecting end of the first shell 206 when the device 200 is in either the first configuration or the second configuration. The projections 242 and indentations 244 create a tactile feel to the user, denoting when the first and second sections 202, 204 are aligned with one another (either in the first configuration or the 180 degree rotated second configuration). Similar to the device 100, the device 200 includes filter paper (not shown) lining the internal surfaces of the first shell 206 under both the cap perforations 216 and the shell perforations 218. The second section 204 of the device 200 has no cap perforations 216 or shell perforations 218, so filter paper is not necessary on an internal surface of the second shell 210. Aside from this difference, the internal cavity of the second section 204 is similar to the internal cavity of the first section 202. As shown in FIG. 15, the first and second caps 208, 212 can be separated from the first and second shells 206, 210, respectively. Thus, the first and second caps 208, 212 can serve a covering function similar to that of the first and second plugs 110, 116 of the device 100, as described above.

The "sections" and "containers" referred to herein can have one cavity or more than one cavity. For example, the device 100 shown in FIGS. 1-8 and the device 200 shown in FIGS. 9-15 can be modified such that one or both of the first and second sections 102, 202, 104, 204 includes more than one cavity. Multiple cavities can be separated, for example, by interfaces similar to those shown in FIGS. 1-15 between the first and second sections 102, 202, 104, 204. For example, one of the cavities within a section or container can serve as a mixing area while a gas forming ingredient is stored in another cavity within the same section or container. In embodiments having filtered perforations opening to the outside environment, the filtered perforations can open to certain cavities within a section or container and not to other cavities within the same section or container. For example, some disclosed embodiments include first and second sections or containers each including a cavity with no filtered openings. These cavities can be used to store gas forming ingredients. In addition, one of the sections or containers can include a cavity with filtered openings to release gas formed after the gas forming ingredients are mixed. If the cavity with filtered openings is within the second section or container, for example, activating the device can include rotating the first section or container and rotating a portion of the second section or container. The rotated portion of the second section or container can be a portion including the cavity containing the gas forming ingredient or a portion including the cavity with filtered openings.

Figure 16:
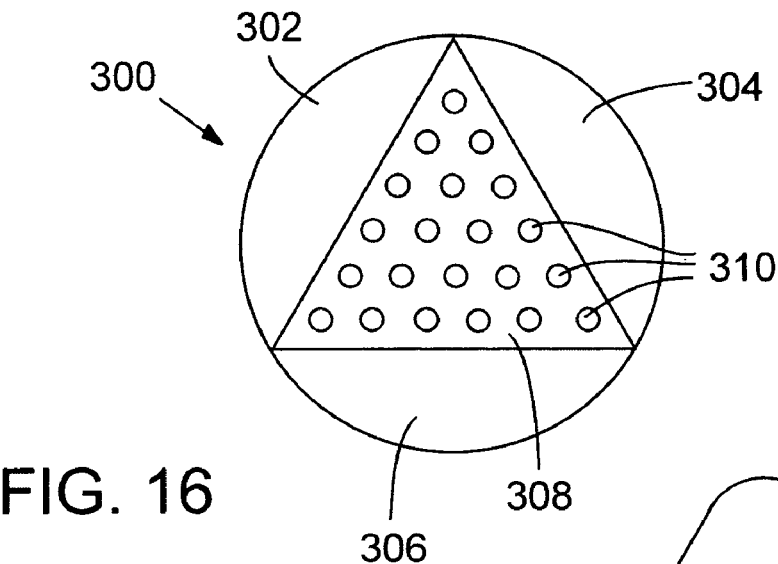
FIG. 16 is a schematic plan view of a third embodiment of the disclosed storage and mixing device with three storage sections, one mixing section, and a rounded overall perimeter.
Figure 17:
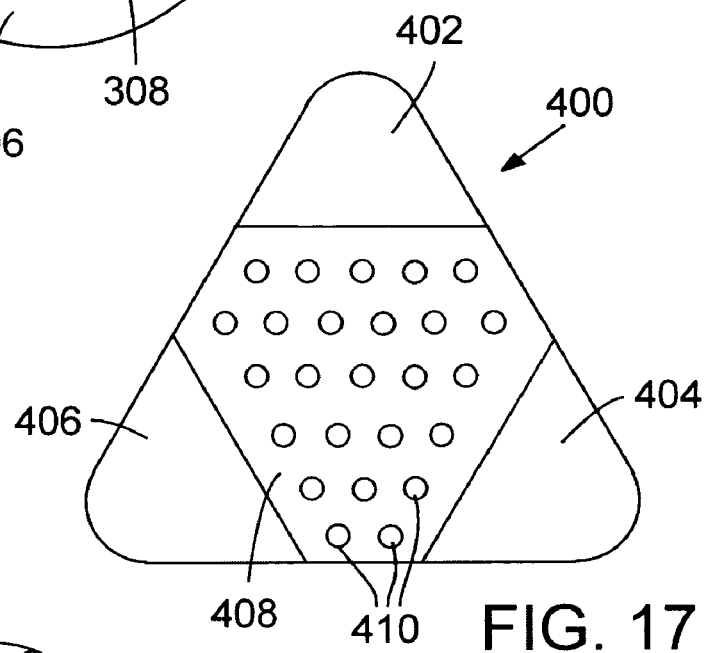
FIG. 17 is a schematic plan view of a fourth embodiment of the disclosed storage and mixing device with three storage sections, one mixing section, and a triangular overall perimeter.

Embodiments of the disclosed device also can include more than two storage cavities. FIGS. 16 and 17 are schematic plan views of two such embodiments. The devices 300, 400 illustrated in FIGS. 16 and 17 each include a first storage section 302, 402, a second storage section 304, 404, a third storage section 306, 406, and a mixing section 308, 408, each with an internal cavity. In the devices 300, 400, the interfaces between each of the storage sections 302, 402, 304, 404, 306 406 and the respective mixing section 308, 408 are similar in structure to the interfaces described above with regard to the device 100 of FIGS. 1-8 and the device 200 of FIGS. 9-15. As in these embodiments, the devices 300, 400 can be activated by rotating each storage section 302, 402, 304, 404, 306 406 one hundred eighty (180) degrees from the configurations shown in FIGS. 16 and 17. This causes openings at the interfaces between each of the storage sections 302, 402, 304, 404, 306 406 and the respective mixing section 308, 408 to become aligned, allowing the contents of each storage section to enter the respective mixing section. Unlike the embodiments shown in FIGS. 1-15, the devices 300, 400 shown in FIGS. 16 and 17 include perforations 310, 410 in the mixing sections 308, 408 only, allowing each of the storage sections 302, 402, 304, 404, 306 406 to be substantially sealed prior to activation.

Figure 18:
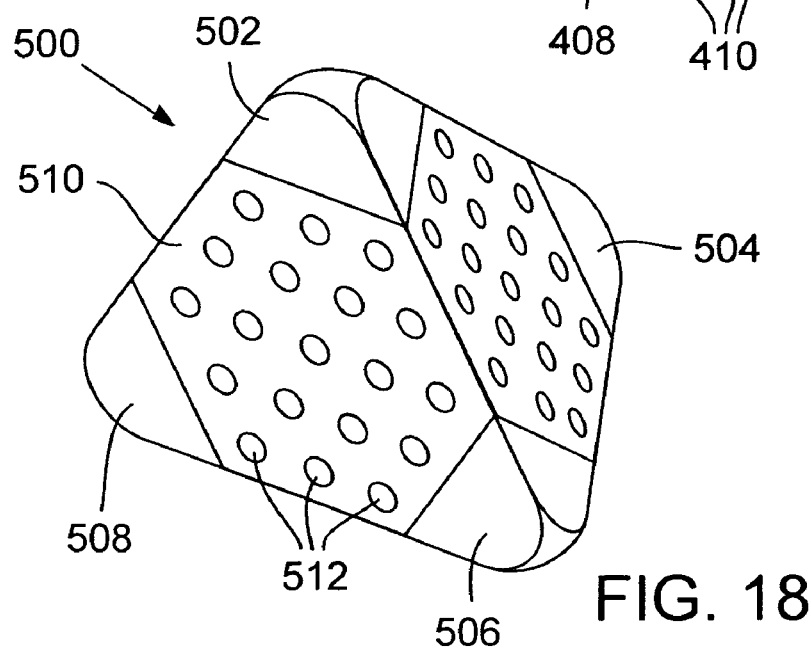
FIG. 18 is a schematic perspective view of a fifth embodiment of the disclosed storage and mixing device with four storage sections, one mixing section, and a tetrahedral overall shape.

FIG. 18 is a schematic perspective view of yet another embodiment of the disclosed device. The device 500 shown in FIG. 18 is shaped substantially as a tetrahedron. The device 500 includes a first storage section 502, a second storage section 504, a third storage section 506, a fourth storage section 508, and a mixing section 510, each with an internal cavity. Perforations 512 are included on each of the four sides of the mixing section 510. Unlike the embodiments shown in FIGS. 1-17, in the device 500, the sides of each storage section 502, 504, 506, 508 become aligned with the sides of the mixing section 510 in three different positions (rather than two). The openings at the interface between each of the storage sections 502, 504, 506, 508 and the mixing section 510 can be sized and shaped accordingly. For example, rather than being shaped substantially as semicircles (as in the devices 100, 200), the openings can be shaped substantially as wedges encompassing approximately one third of a circle. These openings can be positioned in adjacent disks similar to the end portions of the cylindrical projections 130, 224 and the cylindrical recesses 132, 226 of the devices 100, 200. The remaining two thirds of these disks can be solid. Alternatively, in one of the disks, the remaining two thirds can be solid and in the other disk, one third can be solid and one third can be partially open (e.g. grated): This latter configuration would allow the three positions of each storage section 502, 504, 506, 508 to represent closed, partially open and fully open configurations, respectively. The partially open configuration can be used, for example, to regulate the flow of media into the mixing section 510.

As demonstrated by the embodiments described above, the disclosed storage and mixing device can have many different shapes. For example, the embodiments shown in FIGS. 1-8 and 16 are shaped substantially as oblate spheroids, the embodiment shown in FIGS. 9-15 is shaped substantially as an oblate cylindroid, the embodiment shown in FIG. 17 is triangular, and the embodiment shown in FIG. 18 is shaped substantially as a tetrahedron. In other embodiments, the device may substantially resemble some other shape, such as a prolate spheroid, a prolate cylindroid, a sphere, a hemisphere, a cylinder, a half-cylinder, a pyramid or a cube. Typically, embodiments of the device are at least partially rounded in shape. For example, the device 500 shown in FIG. 18 has substantially rounded corners. Other embodiments, however, may have only sharp corners and substantially resemble polyhedrons. The device can be any size, but typically is compact and handheld. For example, the device can have a total volume between about 5 cm$^3$ and about 5000 cm$^3$, such as between about 10 cm$^3$ and about 1000 cm$^3$ or between about 15 cm$^3$ and about 200 cm$^3$.

In some embodiments of the disclosed storage and mixing device, including the embodiments illustrated in FIGS. 1-18, the opposing faces of adjacent sections are not perfectly round. As a result, rotating one section relative to an adjacent section causes the perimeters of the faces of the adjacent sections to move out of alignment and then back into alignment. The perimeters are substantially aligned only while the device is in one of a particular number of configurations (e.g., two configurations separated by 180 degrees of rotation in the devices 100, 200, 300 and 400 shown in FIGS. 1-17 or three configurations separated by 120 degrees of rotation in the device 500 shown in FIG. 18). This encourages the end user to maintain the device in one of these configurations, rather than in an intermediate configuration. The configurations can include, for example, an inactive configuration (e.g., a storage configuration) and an active configuration (e.g., a mixing configuration). The function of the device can be switched by rotating one or more sections (or portions of sections) relative to one or more adjacent sections (or portions of sections).

Embodiments of the disclosed device can serve a variety of functions. For example, some embodiments can be used to separately store two or more different types of media and then allow the media to be mixed on demand. The media can include chemical reactants that produce, for example, warming, cooling or formation of particular reaction products when mixed. In typical embodiments, the media is substantially solid and produces a gaseous reaction product when mixed. Unlike conventional storage and mixing devices, some embodiments of the disclosed device are designed to separately store substantially solid media and then allow the release of a gaseous reaction product after the media has been mixed. The media can be preloaded into the device so that an end user need only activate the device to mix the media and generate the gaseous product. Activating the device can include, for example, rotating one container relative to another container to open a passage between the containers and agitating the device to promote mixing.

Chlorine dioxide, carbon dioxide, and hydrogen peroxide are three examples of useful gases that can be generated in the manner described above. Reactants that can be used to produce these gases are described, for example, in U.S. Pat. Nos. 5,278,112, 5,314,852, 5,464,598, 5,567,405, 5,573,743, 5,730,948, 5,776,850, 5,853,689, 5,883,739, 5,885,543, 6,174,508, 6,379,643, 6,423,277, 6,423,289, 6,458,735, 6,503,419, and 7,087,190, which are incorporated herein by reference. Chlorine dioxide gas has long been used for large-scale bleaching and disinfection, but its utility for small-scale applications has not been appreciated. When generated in small quantities, chlorine dioxide gas is safe enough for use by ordinary consumers. Small quantities of chlorine dioxide gas can be used, for example, to deodorize and/or disinfect household items, such as shoes, gym bags, and drawers, as well as spaces, such as closets and bathrooms.

Reactants for generating products, such as chlorine dioxide gas, often are sensitive to contact with the ambient environment. For example, some solid reactants used to produce chlorine dioxide gas become deactivated by prolonged exposure to atmospheric moisture. Thus, some embodiments of the disclosed device include at least one cavity that can be substantially sealed until the device is activated and the reactants are mixed. For example, in the device 100 illustrated in FIGS. 1-8, the internal cavity of the second section 104 includes no perforations 120 and, thus, is substantially sealed. For additional sealing, the second face plate 112 and the second plug 116 can be welded to the second shell 114 so that the only opening into the internal cavity is the second opening 146. When the device 100 is moved into the second configuration, the first and second openings 144, 146 are aligned so that the media in the internal cavities of the first and second sections 102, 104 can be mixed. A gaseous product then can escape the device 100 via the perforations 120 in the first shell 108.

Some embodiments of the disclosed device are configured so as to maximize the area through which the gaseous product can exit into the atmosphere regardless of the orientation of the device. For example, the device 100 shown in FIGS. 1-8 is shaped to lie with its long axis in the horizontal plane. As shown in FIG. 5, in this orientation, substantially all of the perforations 120 on the top and bottom sides of the first shell 108 are not blocked from releasing gas into the surrounding atmosphere. The same is true in the vertically opposite orientation. With the device 200 shown in FIGS. 9-15, gas can escape through the cap perforations 216 regardless as to whether the shell perforations 218 are facing upward or downward. Thus, both the device 100 and the device 200 can be thrown onto a flat surface and always have at least some (and preferably most or all) of their gas exit points unobstructed. In certain alternative embodiments, some or all of the dimples 118, 214 of the devices 100, 200 shown in FIGS. 1-8 and FIGS. 9-15, respectively, can be replaced with perforations.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A handheld storage and mixing device, comprising first and second separate containers each defining a distinct internal cavity, the first container being rotatable relative to the second container between a first position in which the cavities are substantially sealed from one another and a second position in which a first gas forming ingredient in one of the cavities can mix with a second gas forming ingredient in the other cavity to form a gas, the device further comprising one or more filtered openings to allow the gas to escape into the ambient environment, wherein the first and second containers have opposing faces with non-circular perimeters, the face of the first container covers substantially all of the face of the second container when the first container is in the first position relative to the second container and when the first container is in the second position relative to the second container, and portions of the face of the second container are uncovered when the first container is rotated relative to the second container between the first position and the second position.

2. The handheld storage and mixing device according to claim 1, wherein in the first position one of the first and second containers is substantially sealed against air infiltration and the other of the first and second containers includes the one or more filtered openings.

3. The handheld storage and mixing device according to claim 1, wherein the one or more filtered openings are positioned on a rounded surface.

4. The handheld storage and mixing device according to claim 1, wherein the device is substantially shaped as an oblate spheroid.

5. The handheld storage and mixing device according to claim 1, wherein the device is substantially shaped as a cylinder and the one or more filtered openings are positioned on an end of the cylinder.

6. The handheld storage and mixing device according to claim 1, wherein each of the first and second containers has an outer surface with an alignment indicator, the alignment indicators are substantially coplanar when the first container is in one of the first and second positions, and the alignment indicators are substantially non-coplanar when the first container is in the other of the first and second positions.

7. The handheld storage and mixing device according to claim 1, wherein the first container is permanently attached to the second container at an axis of rotation.

8. The handheld storage and mixing device according to claim 1, wherein the first gas forming ingredient is disposed in the first cavity and the second gas forming ingredient is disposed in the second cavity.

9. The handheld storage and mixing device according to claim 8, wherein the first and second gas forming ingredients cannot be accessed without breaking the device.

10. The handheld storage and mixing device according to claim 8, wherein the first and second gas forming ingredients can be mixed to form chlorine dioxide gas.

11. The handheld storage and mixing device according to claim 1, wherein each of the opposing faces of the first and second containers has an opening, in the first position the openings are substantially non-overlapping, and in the second position the openings are substantially overlapping.

12. The handheld storage and mixing device according to claim 11, wherein one of the opposing faces includes a cylindrical projection sized to fit within a corresponding cylindrical recess in the other of the opposing faces, and the openings are positioned on respective end portions of the cylindrical projection and the cylindrical recess.

13. The handheld storage and mixing device according to claim 12, further comprising an o-ring positioned around a side portion of the cylindrical projection.

14. A handheld storage and mixing device, comprising:
a first container having a first face which defines a first opening; and
a second container having a second face which defines a second opening, wherein the first container is connected to the second container with the first face substantially parallel to the second face, the first and second containers being rotatable relative to one another between a first position in which a perimeter of the first face is substantially aligned with a perimeter of the second face, the first opening is out of alignment with the second opening, and an internal cavity of the first container is separate from an internal cavity of the second container, and a second position with one of the containers rotated 180 degrees relative to the other container in which the perimeter of the first face again is substantially aligned with the perimeter of the second face, the first opening is substantially aligned with the second opening, and the internal cavity of the first container is open to the internal cavity of the second container, the perimeters of the first and second faces being out of alignment with one another when not in the first or second positions.

15. The handheld storage and mixing device according to claim 14, wherein an outside wall of the device is perforated.

16. The handheld storage and mixing device according to claim 14, wherein the first container and the second container are substantially shaped as respective halves of an oblate spheroid.

17. The handheld storage and mixing device according to claim 14, further comprising one or more filtered openings, wherein in the first position one of the first and second containers is substantially sealed against air infiltration and the other of the first and second containers includes the one or more filtered openings.

18. The handheld storage and mixing device according to claim 14, wherein each of the first and second containers has an outer surface with an alignment indicator, the alignment indicators are substantially coplanar when the first container is in one of the first and second positions, and the alignment indicators are substantially non-coplanar when the first container is in the other of the first and second positions.

19. The handheld storage and mixing device according to claim 14, wherein the first container is permanently attached to the second container at an axis of rotation.

20. The handheld storage and mixing device according to claim 14, wherein a first gas forming ingredient is disposed in the internal cavity of the first container and a second gas forming ingredient is disposed in the internal cavity of the second container.

21. The handheld storage and mixing device according to claim 20, wherein the first and second gas forming ingredients cannot be accessed without breaking the device.

22. The handheld storage and mixing device according to claim 20, wherein the first and second gas forming ingredients can be mixed to form chlorine dioxide gas.

23. The handheld storage and mixing device according to claim 14, wherein the first face and the second face each have an opening, in the first position the openings are substantially non-overlapping, and in the second position the openings are substantially overlapping.

24. The handheld storage and mixing device according to claim 23, wherein one of the first and second faces includes a cylindrical projection sized to fit within a corresponding cylindrical recess in the other of the first and second faces, and the openings are positioned on respective end portions of the cylindrical projection and the cylindrical recess.

25. The handheld storage and mixing device according to claim 24, further comprising an o-ring positioned around a side portion of the cylindrical projection.

* * * * *